United States Patent [19]
Fitz

[11] Patent Number: 6,146,415
[45] Date of Patent: Nov. 14, 2000

[54] STENT DELIVERY SYSTEM

[75] Inventor: Matthew J. Fitz, Sunnyvalle, Calif.

[73] Assignee: Advanced Cardiovascular Systems, Inc., Santa Clara, Calif.

[21] Appl. No.: 09/307,177

[22] Filed: May 7, 1999

[51] Int. Cl.[7] .................................................. A61F 2/06
[52] U.S. Cl. ......................................... 623/1.11; 606/171
[58] Field of Search .............................. 606/108; 604/264, 604/280, 171; 623/1.11

[56] References Cited

U.S. PATENT DOCUMENTS

| | | |
|---|---|---|
| 5,025,778 | 6/1991 | Silverstein et al. ..................... 600/104 |
| 5,026,377 | 6/1991 | Burton et al. . |
| 5,190,058 | 3/1993 | Jones et al. . |
| 5,201,757 | 4/1993 | Heyn et al. . |
| 5,261,889 | 11/1993 | Laine et al. .............................. 604/164 |
| 5,290,295 | 3/1994 | Querals et al. . |
| 5,391,172 | 2/1995 | Williams et al. . |
| 5,458,605 | 10/1995 | Klemm .................................... 606/108 |
| 5,507,768 | 4/1996 | Lau et al. . |
| 5,534,007 | 7/1996 | St. Germain et al. .................. 606/108 |
| 5,603,698 | 2/1997 | Roberts et al. .......................... 604/104 |
| 5,690,643 | 11/1997 | Wijay ....................................... 606/108 |
| 5,690,644 | 11/1997 | Yurek et al. ............................. 606/108 |
| 5,817,101 | 10/1998 | Fiedler .................................... 606/108 |

*Primary Examiner*—Paul J. Hirsch
*Assistant Examiner*—Michael B. Priddy
*Attorney, Agent, or Firm*—Fulwider Patton Lee & Utecht, LLP

[57] ABSTRACT

A stent delivery system with a stabilizing manipulator handle is disclosed. The system has a self-expanding stent in a contracted condition disposed on the distal end of a delivery catheter and a retractable sheath covering the stent. The delivery catheter is advanced through a guide catheter to a desired location within a patient's body lumen. The manipulator handle at the proximal end of the delivery catheter is attached to the guide catheter. The handle has a slidable stem connected to the sheath, and features a screw down spacer between the distal end of the handle and the proximal end of the guide catheter. The spacer situates the position of the guide catheter relative to the delivery catheter even during deployment of the stent. Once the stent is at the target site, the sheath is retracted by pulling back on the stem to expose the self-expanding stent. A stop on the interior of the delivery catheter positioned proximal to the stent further prevents the latter from moving out of position when the sheath is retracted.

22 Claims, 6 Drawing Sheets

STENT DELIVERY SYSTEM

BACKGROUND OF THE INVENTION

The present invention relates in general to the delivery of stents into a body lumen, such as a blood vessel, to maintain the patency thereof. More particularly, the present invention relates to an improved stent delivery system which can quickly and accurately position a self-expanding stent into a body lumen.

In a medical procedure known as percutaneous transluminal coronary angioplasty (PTCA), a balloon catheter is used to dilate the lumen of a coronary artery which has become narrowed or restricted due to the accumulation of atherosclerotic plaque along the artery wall. In the PTCA procedure, a balloon catheter is advanced through the vasculature to the stenosis and the balloon is inflated to radially compress the atherosclerotic plaque against the inside of the artery wall. The balloon is then deflated so that the dilation catheter can be removed and blood flow resumed through the dilated artery.

Occasionally, the inflation of the balloon within the artery lumen will dissect either the stenotic plaque or the intima of the blood vessel or both. After the balloon is deflated and removed, blood can flow between the arterial wall and the dissected lining thereby constricting the flow passage or causing a section of the dissected lining, commonly called an "intimal flap," to be forced into the flow passageway. In the event of partial or total occlusion of a coronary artery by a dissected arterial lining, the patient is put in an extremely dangerous situation requiring immediate medical attention, particularly when the occlusion occurs in one of the coronary arteries.

Another problem which frequently arises after an angioplasty procedure is the appearance of a restenosis at or near the site of the treated artery. The restenosis may appear due to the accumulation of additional atherosclerotic plaque or may be the result of weakened arterial walls which have collapsed inward to restrict blood flow. When restenosis appears, the treated patient may require an additional angioplasty procedure or other treatment such as by-pass surgery, if an additional angioplasty procedure is not warranted.

Due to the problems caused by dissections of the arterial lining or the appearance of restenosis, much research has been performed on ways to maintain the patency of an artery after the angioplasty procedure is completed. In recent years, expandable endoprosthetic devices, commonly called "stents," have gained widespread acceptance as a means to support the arterial walls and maintain the patency of a treated vessel. Stents are generally cylindrically shaped intravascular devices which are placed within a damaged artery to hold it open and maintain unimpeded blood flow. Stents prevent dissected arterial linings from occluding an artery by pressing the dissected tissue against the arterial wall until natural healing results in the re-securing of the dissected tissue to the arterial wall. Stents also prevent the appearance of restenosis in the treated vessel by supporting the weakened arterial walls.

Various means have been developed for delivering and implanting intravascular stents within a body lumen. One common method involves compressing or otherwise reducing the diameter of a self-expanding stent, mounting the compressed stent on the distal end of a delivery catheter, placing a tubular sheath over the stent to restrain the stent in the contracted condition, and advancing the catheter through the patient's vasculature to the desired location. Once the stent is properly positioned, the stent is exposed by withdrawing the sheath proximally with respect to the stent, advancing the stent distally with respect to the sheath, or performing a combination of both. Once free from the sheath, the self-expanding stent expands against the arterial walls to thereby hold open the artery or other body lumen into which it is placed.

Other examples of stent delivery systems include U.S. Pat. No. 5,026,377 to Burton et al. Burton discloses an instrument for the deployment or retraction of a self expanding stent in a body canal, which comprises an elongated tubular outer sleeve having disposed therein an elongated core which is moveable relative to the sleeve and has a grip member formed at or near its distal end, which grip member is adapted to releasably hold a self-expanding stent within the outer sleeve. U.S. Pat. No. 5,190,058 to Jones et al. discloses a method of using a temporary stent catheter. The catheter comprises a catheter tube having a distal end and a proximal end; an elongated balloon inflatable by fluid pressure attached to the catheter tube near its distal end; a stent having a tubular configuration attached to the catheter tube near its distal end and surrounding the balloon; a pressurization device near the proximal end of the catheter tube for inflating and deflating the balloon, whereby the stent may be pressed against the wall of a blood vessel by the balloon and the balloon may be subsequently deflated; a restriction device near the proximal end of the catheter tube for maintaining the stent in an expanded condition and for subsequently effecting the radial contraction of the stent whereby it may be removed from the blood vessel.

U.S. Pat. No. 5,201,757 to Heyn et al. discloses an apparatus for deploying a radially self-expanding stent that includes proximal and distal sleeves respectively containing proximal and distal end portions of the stent in a reduced radius delivery configuration. Once the stent and sleeves are positioned at the intended fixation site, the sleeves are moved axially with respect to one another to permit radial self-expansion of the stent only over its medial region, while the sleeves continue to contain the axially outward regions of the stent. Upon sufficient movement of the sleeves axially relative to one another, the stent becomes totally free of the sleeves. U.S. Pat. No. 5,290,295 to Querals et al. discloses a tool for the intraluminal insertion and deployment of a tubular graft within a blood vessel, which is constructed from a flexible insertion shaft with a tapered distal end, a tubular sheath, a deployment slider, and a safety locking tube.

U.S. Pat. No. 5,391,172 to Williams et al. discloses a stent delivery system with coaxial catheter handle. The catheter handle provides relative motion between the outer sheath of a stent delivery catheter and an underlying catheter, via a thumb switch, to enable the outer sheath to withdraw from over the underlying catheter and expose a vascular prosthesis.

U.S. Pat. No. 5,507,768 to Lau et al. discloses a stent delivery method and system that includes an elongated delivery sheath and a catheter disposed within an outer lumen of the sheath having an expandable member on its distal extremity. An expandable stent is mounted on the expandable member, the distal portion of the sheath tapers down and is tucked within an elastic cone during transport of the stent to a stenotic region. A manipulating device is provided on the proximal end of the delivery system to effect relative axial movement between the sheath and the catheter so as to expose the stent mounted on the expandable member on the catheter within a body lumen such as a coronary artery and allow the expansion of the stent by the expansion of the expandable member.

One of the difficulties with some prior art self-expanding stents involves deploying the stent at the precise, desired location within the body lumen. Typically, a self-expanding stent is mounted on the distal end of a delivery catheter which is attached to a manipulator handle outside the patient's body. The stent is deployed by actuating a mechanism on the manipulator handle, such as a thumb plate, which is hand operated by the physician. When the thumb plate is withdrawn proximally relative to the manipulator handle, the sheath is withdrawn proximally relative to the catheter and stent.

The problem arises when the operator applies a proximal force to move the thumb plate, a counteracting distal force is normally applied to the manipulator handle thereby making it very difficult to hold the manipulator handle steady. If the handle is inadvertently moved while the sheath is retracted, the stent may not be deployed in the desired location. As a result, the ends of the stent may damage the vessel by pushing into the vessel wall. In addition, a poorly placed stent may do more harm than good and can be very difficult to retrieve once deployed. Therefore, it is critical to position the stent accurately on the first attempt.

What has been needed and heretofore unavailable is a delivery system for self-expanding stents which provides a means to fix the position of the manipulator handle during the stent deployment process to prevent unwanted movement and to provide greater accuracy of stent placement within a body lumen. The present invention satisfies this need.

SUMMARY OF THE INVENTION

The present invention is directed to a stent delivery system which provides for improved accuracy of stent placement within a body lumen by preventing unwanted axial movement of the manipulator handle during the delivery and deployment of a self-expanding stent. The present invention in a preferred embodiment comprises an elongated catheter body having an inner lumen extending therein which is adapted to receive a guidewire. A cylindrically shaped, self-expanding intravascular stent is slidably disposed on the exterior of the distal end of the catheter. The catheter and stent are slidably disposed within the lumen of an elongated tubular sheath formed at the distal end to receive telescopically the self-expanding stent and to hold it in a contracted condition during delivery. A manipulator handle is attached to the proximal end of the catheter and includes a slidable element which is connected to the proximal end of the tubular sheath. A guide catheter is provided to facilitate advancement of the delivery assembly through the patient's vasculature to the treatment site.

Once the stent is delivered to the desired location within the patient's vasculature, a coupling device on the manipulator handle allows the operator to fix the axial position of the manipulator handle relative to the guide catheter. The coupling device may be in the form of an adjustable length arm which releasably attaches the manipulator handle to the guide catheter thereby anchoring the axial position of the manipulator handle. With the manipulator handle anchored to the guide catheter, the operator may retract the sheath by withdrawing the slidable switch without being concerned about inadvertently moving the manipulator handle in the process. Therefore, the operator may focus on the stent deployment rather than on holding the manipulator handle steady.

In a typical procedure, a guide catheter is percutaneously introduced into the patient's arterial system and is advanced until the distal tip of the catheter is disposed in the ostium of a coronary artery. The stent delivery system and a guidewire which is slidably disposed within the lumen of the catheter are advanced through the guide catheter to the distal end thereof. The guidewire is advanced out of the distal tip of the guide catheter into the patient's coronary anatomy until the distal tip of the guidewire reaches the desired arterial location. The stent delivery system is then advanced over the guidewire until the stent reaches the desired position. A coupling device is used to attach the manipulator handle to the proximal end of the guide catheter such that the manipulator handle is prevented from moving relative to the guide catheter. The sheath is then withdrawn proximally by pulling back on the slidable switch located on the manipulator handle to expose the self-expanding stent. A stop may be located on the catheter just proximal of the stent to prevent the stent from sliding proximally relative to the catheter due to frictional engagement with the sheath. When the sheath is retracted, the self-expanding stent located on the distal end of the catheter is exposed thereby allowing the stent to expand against the vessel wall.

Because the manipulator handle is attached to the guide catheter, the axial position of the catheter and the stent are not affected while manipulating the switch on the manipulator handle to retract the sheath. The coupling device holds the catheter steady during deployment and ensures that the stent will expand in the desired position within a body lumen.

The stent delivery system can be used to accurately deliver a stent to a desired location within a patient's vasculature system or other body lumen by preventing unwanted axial motion of the self-expanding stent during the deployment process. The stent delivery system is safe, easy to use and can be quickly and easily removed after the stent has been deployed. The present invention is designed primarily for use in coronary arteries, however, it may also be used to treat other vessels including the renals, abdominal aorta, femoral, and carotid arteries. Other features and advantages of the present invention will become apparent from the following detailed description, taken in conjunction with the accompanying drawings, which illustrate, by way of example, the features of the invention.

DETAILED DESCRIPTION OF THE PREFERRED EMBODIMENTS

As shown in the drawings for purposes of illustration, the present invention is directed to a stent delivery system having a manipulator handle coupled to a guide catheter during stent deployment thereby allowing for more accurate stent positioning within a body lumen. Frequently, after balloon angioplasty has been performed to dilate a stenosis in the lumen of a vessel, a self-expanding stent is deployed at the treated site to aid in the healing of dissected arterial lining and to prevent restenosis.

Typically, a self-expanding stent is delivered and deployed by first compressing the stent, mounting the stent at the distal end of a delivery catheter and slidably disposing the catheter and stent within the lumen of a sheath to hold the stent in a contracted condition. Once the catheter and stent are advanced to the desired location within a body lumen, the sheath is retracted to expose the self-expanding stent thereby allowing it to expand against the vessel wall. Examples of stent delivery systems are disclosed in, for example, U.S. Pat. No. 5,391,172 to Williams et al., and U.S. Pat. No. 5,507,768 to Lau et al., whose entire contents are hereby incorporated by reference.

Some conventional stent delivery systems have limitations, because the axial position of the stent might shift within the body lumen while the physician is actuating a switch on the manipulator handle to retract the sheath from the stent. Stent deployment requires precise positioning to be effective. It is therefore an object of the present invention to solve the accuracy problems associated with the prior art method of delivering and deploying self-expanding stents.

Figures 1, 2, 3, 4:
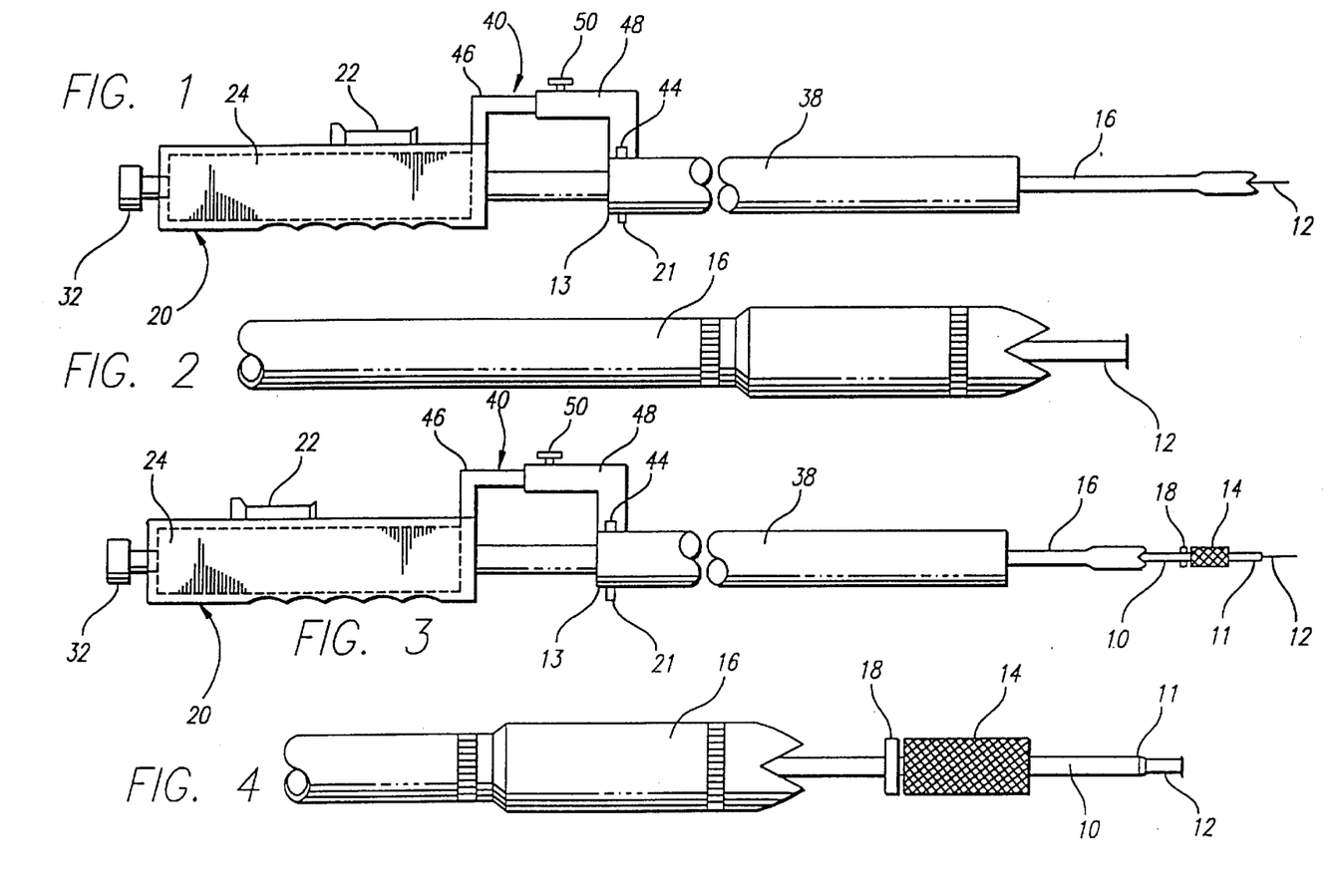
FIG. 1 is a side elevational view of a preferred embodiment stent delivery system of the present invention.
FIG. 2 is a partial and magnified side elevational view of the distal end of the stent delivery system depicted in FIG. 1.
FIG. 3 is a side elevational view similar to FIG. 1, but showing the sheath in its withdrawn position.
FIG. 4 is a partial and magnified view of the distal end of the stent delivery system depicted in FIG. 3.

FIGS. 1–11 illustrate an exemplary stent delivery system that embodies features of the present invention. In the side elevational views of FIGS. 1–4, the present invention delivery system includes delivery catheter 10 with a lumen, guidewire 12 slidably disposed within a lumen of delivery catheter 10, and self-expanding stent 14 mounted on distal end 11 of catheter 10. As best seen in FIG. 4, delivery catheter 10 preferably has an elongated catheter body with at least one optional stop 18 that is immobile and located on a periphery near distal end 11 but proximal to stent 14 to prevent stent 14 from moving proximally relative to catheter 10. Stop 18 may be an annular protrusion, a simple projection, or the like to block the proximal movement of stent 14.

Catheter 10 and stent 14 are slidably disposed within elongated tubular sheath 16, which holds stent 14 in a contracted condition during advancement through the patient's vasculature. Manipulator handle 20 is provided at the proximal end 13 of the delivery system to effect relative, axial movement between catheter 10 and sheath 16. FIGS. 1 and 2 show the delivery system as it exists during advancement through the vasculature with sheath 16 at least partially covering stent 14. FIGS. 3 and 4 show the delivery system after sheath 16 has been withdrawn proximally relative to catheter 10 to expose self-expanding stent 14.

Figure 5:
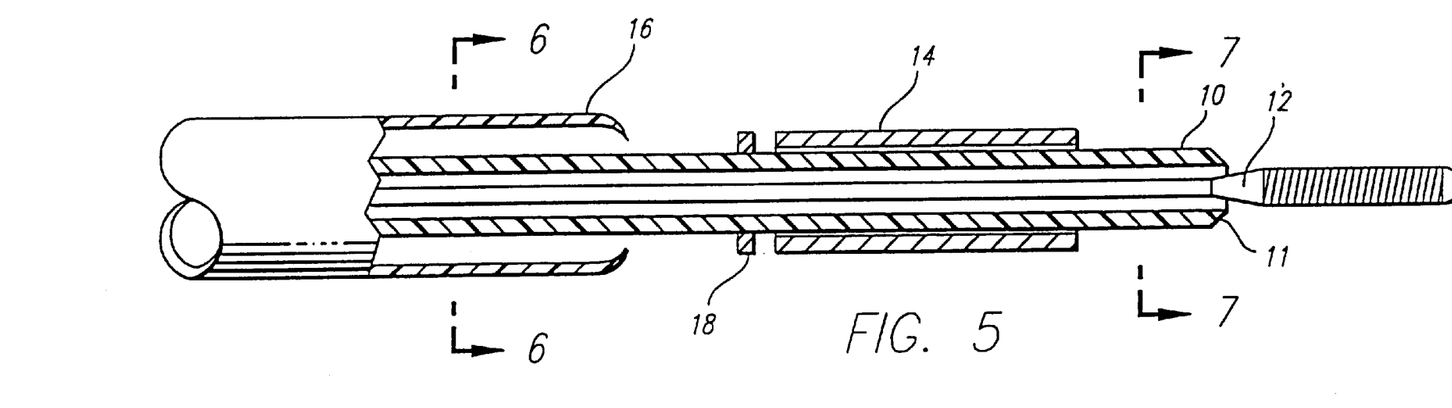
FIG. 5 is a cross-sectional view of the distal end of the stent delivery system as shown in FIG. 3 with the sheath withdrawn from the stent.
Figure 6:
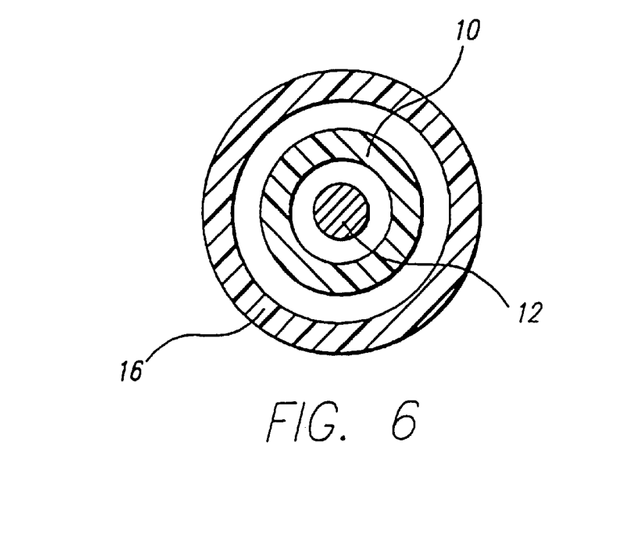
FIG. 6 is a cross-sectional view taken along line 6—6 of FIG. 5 depicting the catheter and guidewire contained within a lumen of the sheath.
Figure 7:
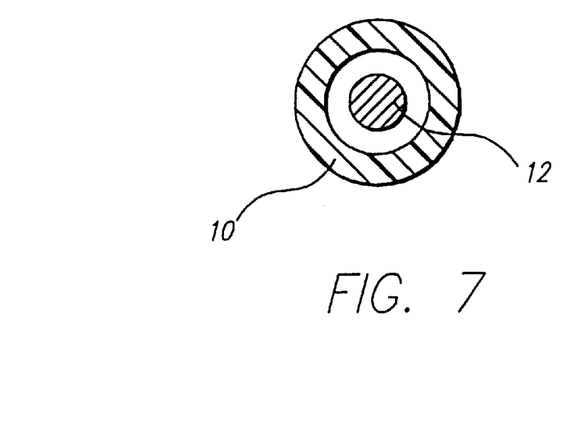
FIG. 7 is a cross-sectional view taken along line 7—7 in FIG. 5 depicting the guidewire slidably disposed within the catheter lumen.

FIG. 5 is a cross-sectional view of distal end 11 of the delivery system after sheath 16 has been withdrawn to expose stent 14. FIGS. 6 and 7 show cross-sections of the delivery system wherein guidewire 12 is contained within the lumen of catheter 10 and catheter 10 is contained within a lumen of sheath 16.

Figures 8, 9, 10:
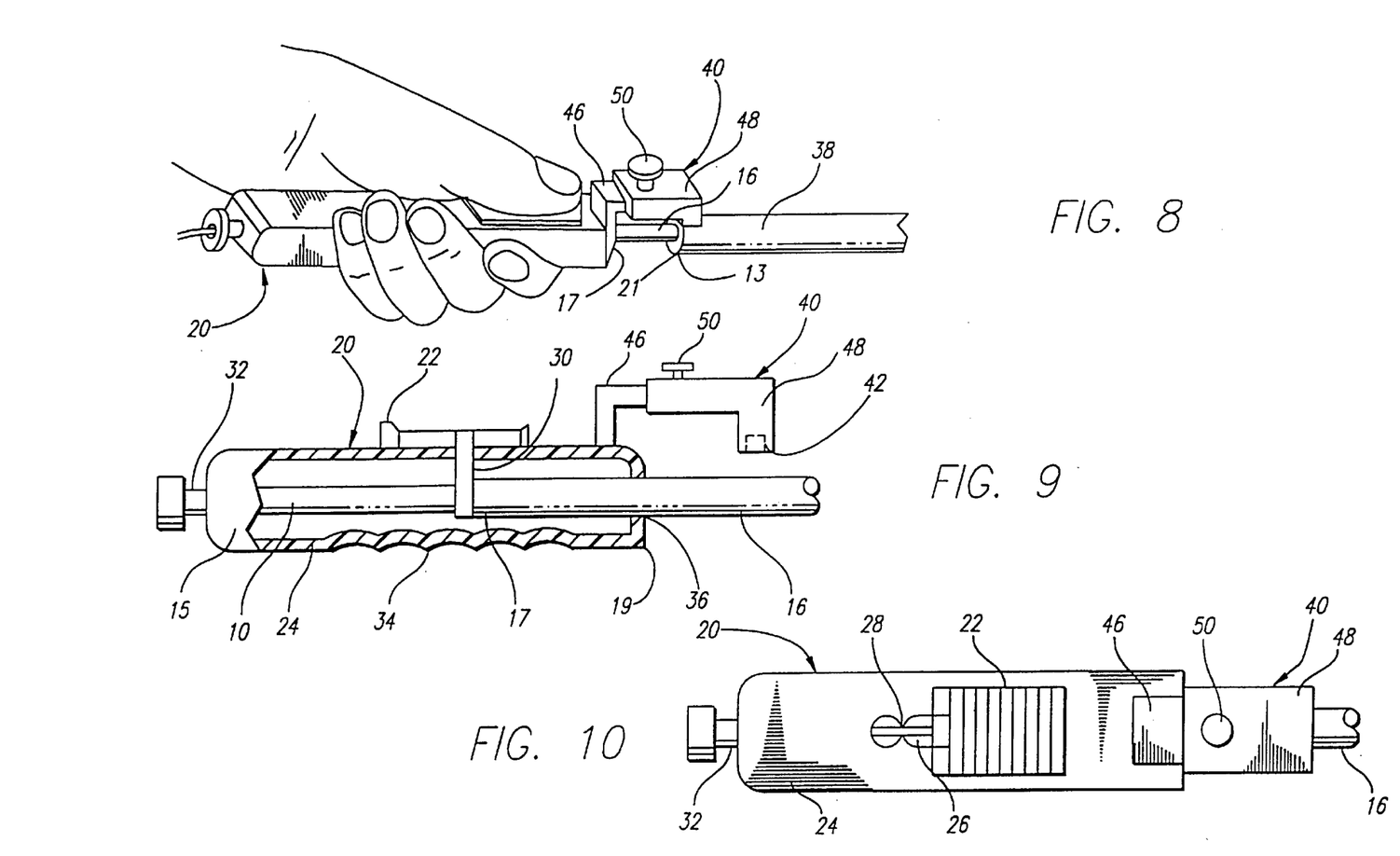
FIG. 8 is a partial perspective view of the manipulator handle included in the preferred embodiment stent delivery system shown in FIG. 1.
FIG. 9 is a side elevational view, partially in section, of the manipulator handle shown in FIG. 8.
FIG. 10 is a top plan view of the manipulator handle shown in FIG. 8.

FIGS. 8–10 depict a preferred embodiment manipulator handle 20 located at proximal end 17 of the present invention delivery system. Manipulator handle 20 includes slidable element 22 on the exterior of housing 24, which is attached to stem 30. Stem 30 extends through slot 26 in the wall of housing 24 and is secured to proximal end 17 of tubular sheath 16. Stem 30 is received in a close fit relationship through slot 26. As best seen in the plan view of FIG. 10, slot 26 in the wall of housing 24 has narrowed portions 28 near both ends thereof which have widths just slightly smaller than stem 30 such that the position of slidable element 22 can be locked.

Manipulator handle 20 is preferably secured to proximal end 15 of delivery catheter 10 using a means such as a Luer lock 32. Within housing 24 of manipulator handle 20, starting at its proximal end 15, catheter 10 extends distally and enters a lumen at proximal end 17 of tubular sheath 16.

The underside of manipulator handle housing 24 may optionally be provided with undulating surface 34 adapted to receive the fingers of a physician to facilitate gripping thereof. Sheath 16, with catheter 10 slidably disposed in its lumen, emerges from port 36 at distal end 19 of manipulator handle housing 24 and enters the lumen at proximal end 21 of guide catheter 38. Guide catheter 38 facilitates the advancement of the stent delivery system through the a patient's vasculature and has a diameter large enough to allow free longitudinal movement of the stent delivery system therein.

In the preferred embodiment of the present invention depicted in FIGS. 8–10, coupling arm 40 carried on manipulator handle housing 24 releasably attaches to proximal end 21 of guide catheter 38 once the delivery system has been fully advanced and stent 14 is located in the desired axial position within a body lumen. Proximal end 21 of guide catheter 38 may include an optional valve with an O-ring seal (not shown) to help stabilize that end as guide catheter 38 is slidably adjusted over sheath 16.

Coupling arm 40, importantly, provides a means to fix the position of manipulator handle 20 with respect to guide catheter 38. Furthermore, the position of delivery catheter 10 is also fixed relative to the manipulator handle 10. Thus, the position of delivery catheter 10 carrying stent 14 relative to the position of guide catheter 38 is set precisely. This in turn enables precise deployment of stent 14 at the target site.

In order to precisely set the relative catheter positions, coupling arm 40 has optional notch 42 located at the bottom of its distal end which receives tab 44, shown in FIGS. 1 and 2, mounted on the exterior of proximal end 21 of guide catheter 38. Tab 44 may be a Luer tab design. With tab 44 inserted in notch 42, coupling arm 40 prevents manipulator handle 20 from moving relative to guide catheter 38. Of course, the length of coupling arm 40 can be varied using an adjustment means, shown in FIGS. 11–14, to precisely and accurately position stent 14 at the delivery site.

Figure 11:
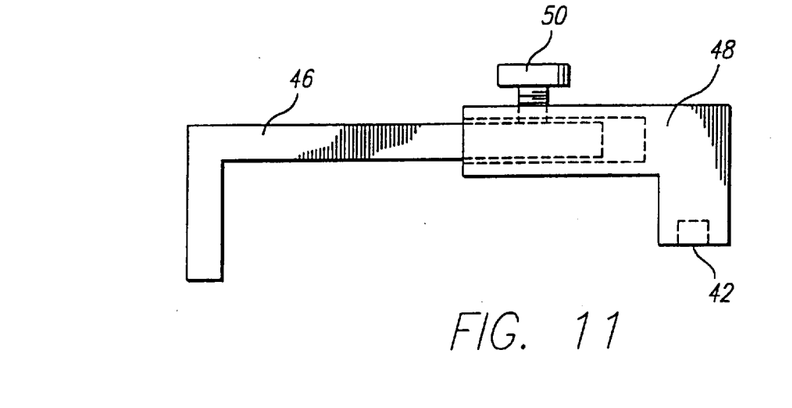
FIG. 11 is a side elevational view of a first embodiment of an attachment device.

FIG. 11 illustrates coupling arm 40 with rigid proximal section 46 and rigid distal section 48. Proximal section 46 is telescopically received within a lumen of distal section 48, and threaded screw 50 is advanced through a port on the top of distal section 48 frictionally engages proximal section 46. The friction prevents relative movement between sections 46, 48.

The dimensions of the present invention delivery catheter generally follows the dimensions of delivery catheters used in angioplasty procedures in the same arterial location. In the preferred embodiment, the length of a catheter for use in the coronary arteries is about 150 cm and the outer diameter of the catheter is about 0.035 inch (0.89 mm). For carotid and other peripheral procedures, the length of the catheter ranges preferably from 60 to 125 cm, with an outside diameter of 0.070 to 0.095 inch.

The tubular sheath is generally shorter than the delivery catheter by approximately the length of the manipulating device. The sheath has preferably an inner diameter large enough to accommodate the delivery catheter and to allow free longitudinal movement therein. The distal end of the sheath preferably has an increased diameter suitable for accommodating the self-expanding stent in a contracted condition. The delivery catheter and sheath can be made of conventional polyethylene tubing, or engineering polymers such as nylon, PEEK (polyethylene ethyl ketone), or PET (polyethylene terephthalate). The manipulator handle and coupling arm can be made of conventional materials such as polycarbonate, nylon, or polystyrene.

In operation, guide catheter 38 is percutaneously introduced into the cardiovascular system of a patient through, for instance, the femoral artery, and is advanced therein until the distal tip thereof is just proximal of the vessel site to be treated. Typically, guide catheter 38 is advanced until it is disposed in the ostium of a coronary artery. The stent delivery system is introduced through guide catheter 38 with guidewire 12 slidably disposed within the lumen of catheter 10. Upon reaching the distal end of guide catheter 38, guidewire 12 is extended out from catheter 10 and is advanced to the target site. Thereafter, catheter 10 and stent 14 are advanced over guidewire 12 by pushing forward on manipulator handle 20 until stent 14 is positioned at the desired location.

Coupling arm 40 carried on manipulator handle 20 is then adjusted in length by rotating screw 50 such that proximal 46 and distal 48 sections of coupling arm 40 are free to move relative to one another. At this point, notch 42 on the coupling arm is placed on to tab 44 located on guide catheter 38 to anchor manipulator handle 20 to guide catheter 38. Screw 50 on coupling arm 40 is then tightened to engage frictionally proximal section 46 of coupling arm 40 and to prevent relative movement between the two sections 46, 48. Once screw 50 is tightened, there cannot be any relative axial movement between manipulator handle 20 and guide catheter 38.

Importantly, as mentioned above, with the position of manipulator handle 20 fixed relative to guide catheter 38, the position of stent 14 mounted on the distal end of delivery catheter 10 is also fixed relative to guide catheter 38, and therefore the two should remain stationary within the body lumen, even during stent deployment. It should be clear that coupling arm 40 serves as a stabilizing component in the present invention stent delivery system.

To deploy self-expanding stent 14, the physician first grasps manipulator handle 20 with the thumb on slidable element 22 and the fingers along undulating surface 36 for secure gripping. The physician then moves slidable element 22 proximally relative to manipulator handle 40 while using a fluoroscope to view the treated site. When slidable element 22 is moved proximally, sheath 16 is withdrawn proximally relative to both catheter 10 and self-expanding stent 14. In the same motion that sheath 16 is withdrawn proximally, stent 14 is prevented from sliding proximally along catheter 10 by at least one immobile stop 18 located on the periphery of catheter 10.

With coupling arm 40 attached to guide catheter 38, the physician is free to push against manipulator handle 20 in order to produce enough force to withdraw slidable element 22 without affecting the axial position of catheter 10 or stent 14. As slidable element 22 is withdrawn, stem 30 passes through the narrowed portion 28 of slot 26 in manipulator handle housing 24 and locks sliding element 22 into the fully withdrawn position.

With sheath 16 withdrawn, self-expanding stent 14 is no longer restrained in a contracted state and expands against the vessel walls. After stent 14 has fully deployed, coupling arm 40 is disconnected from guide catheter 10 and the delivery system is withdrawn from the patient's body with stent 14 remaining in the vessel lumen to maintain the patency of the treated vessel.

Figure 12:
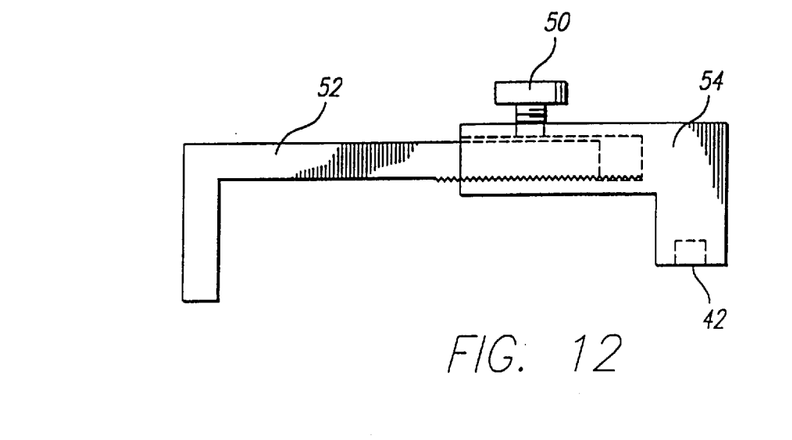
FIG. 12 is a side elevational view of a second embodiment of an attachment device.

FIGS. 12–15 show various alternative embodiments of the coupling arm used to attach manipulator handle 20 to guide catheter 38. FIG. 12 is a second embodiment which is similar to the preferred embodiment, but teeth 56 are provided on the lower portion of proximal section 52 and in the lumen in distal section 54 to further prevent relative motion between the sections 52, 54. Threaded screw 50 is used to secure the sections frictionally.

Figure 13:
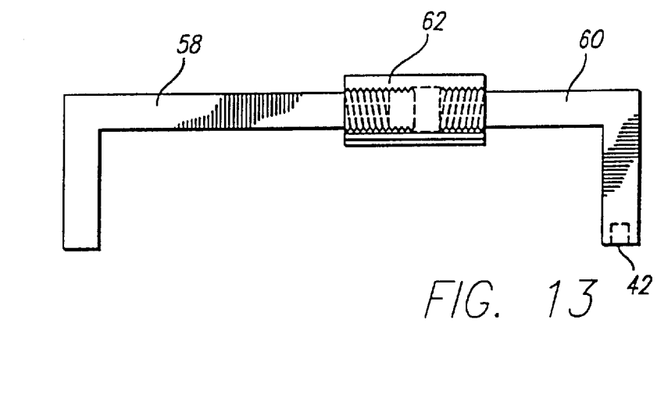
FIG. 13 is a side elevational view of a third embodiment of an attachment device.
Figure 14:
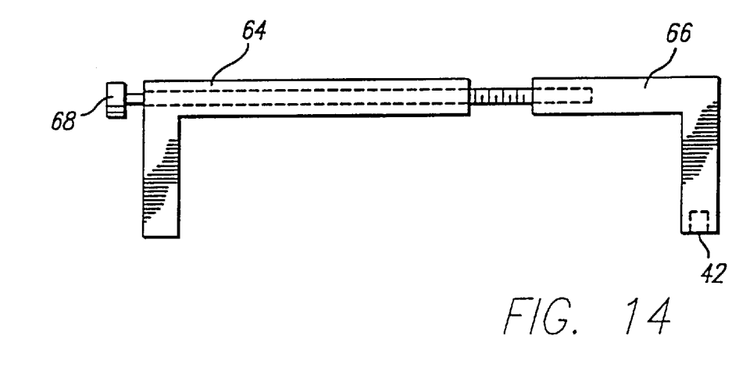
FIG. 14 is an enlarged elevational view of a fourth embodiment of an attachment device.
Figure 15:
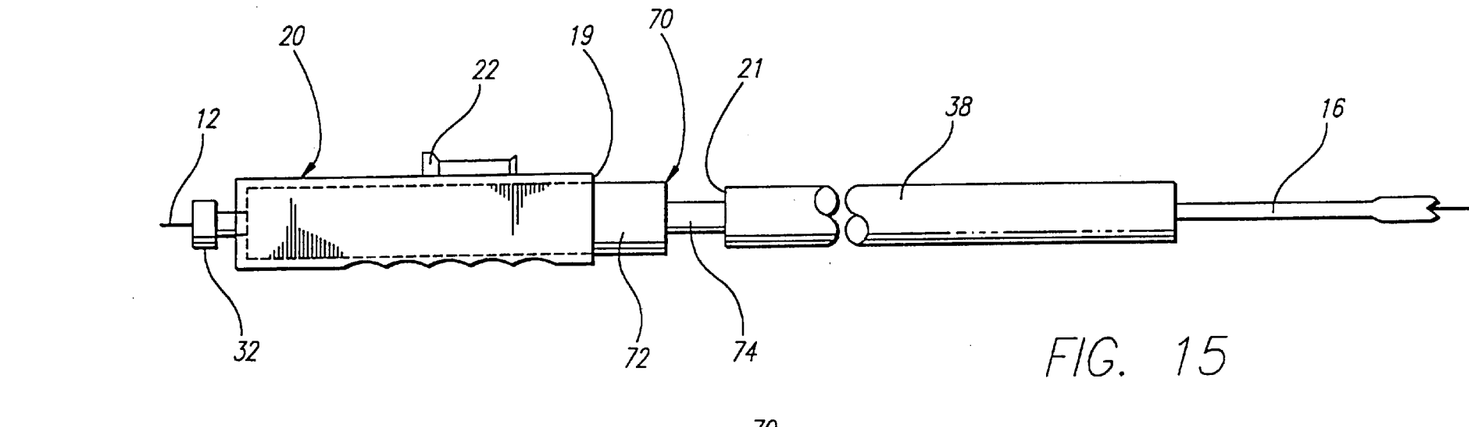
FIG. 15 is a side elevational view of an alternative embodiment of the present invention stent delivery system.

FIG. 13 illustrates a third embodiment coupling arm in which proximal section 58 and distal section 60 of the coupling arm are connected with rotatable member 62. Either or both proximal and distal sections 58, 60 are threaded such that turning rotatable member 62 either draws both sections 58, 60 together or pushes them apart. FIG. 14 illustrates a fourth embodiment coupling arm in which threaded screw 68 extends through a lumen in proximal section 64, out the distal end of the proximal section 64, and into proximal end of distal section 66. Screw 68 cannot be moved axially within proximal portion 64 but may be rotated freely therein to engage threads in distal portion 66. Rotating screw 68 in either direction pulls distal section 66 closer or pushes it away.

In yet another embodiment of the present invention, coupling spacer 70 is provided which extends between manipulator handle 20 and guide catheter 38. As illustrated in the side elevational view of FIG. 15, coupling spacer 70 engages distal end 19 of manipulator handle 20 and proximal end 21 of guide catheter 38 to prevent manipulator handle 20 from moving distally relative to guide catheter 38. Therefore, with coupling spacer 70 in place, a distal force can be applied to manipulator handle 20 without inadvertently moving manipulator handle 20 in the distal direction.

Figure 16:
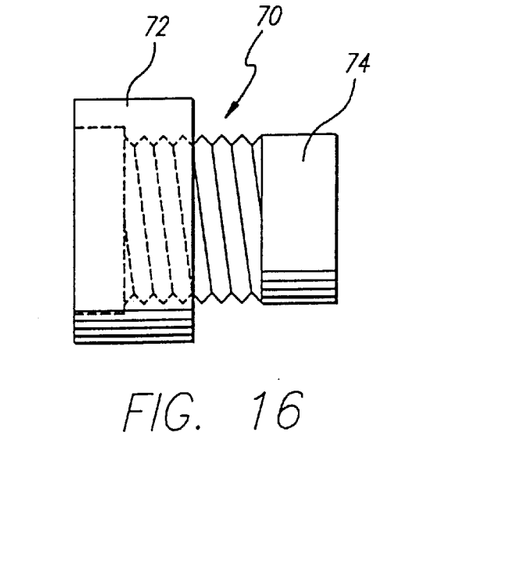
FIG. 16 is a magnified, side elevational view of a telescopically-adjusting spacing element included in the stent delivery system shown in FIG. 15.

Coupling spacer 70 is preferably made of outer tube 72 which telescopically receives inner tube 74. The outer portion of inner tube 74 and the inner portion of outer tube 72 are threaded such that the portions may be rotated relative to one another to adjust the width of the coupling spacer as needed. This is illustrated in the side elevational view of coupling spacer 70 in FIG. 16.

Figure 17:
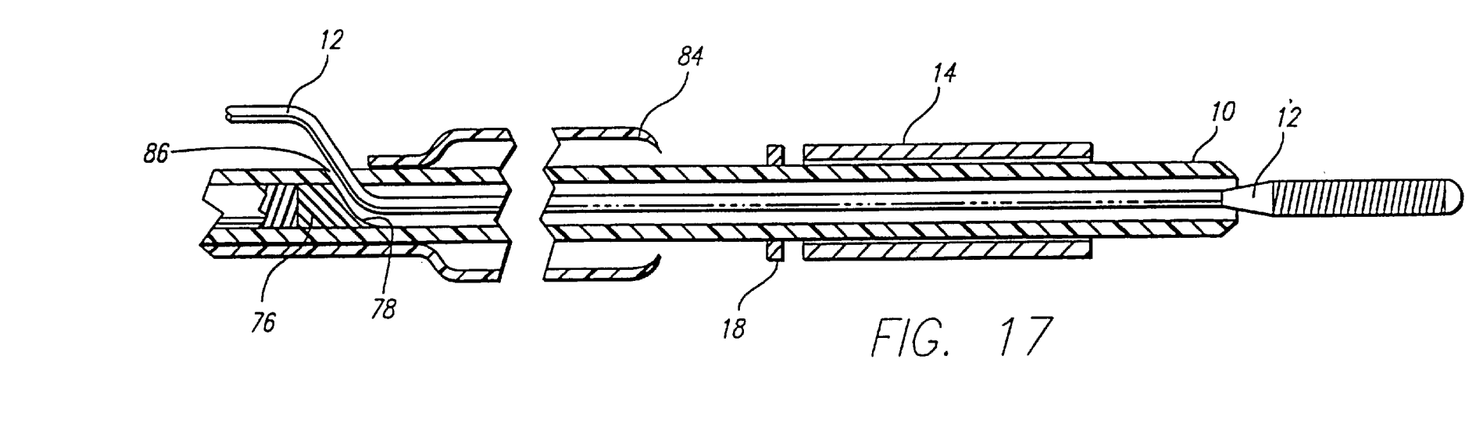
FIG. 17 is a cross-sectional view of the distal end of an alternative embodiment stent delivery system.
Figure 18:
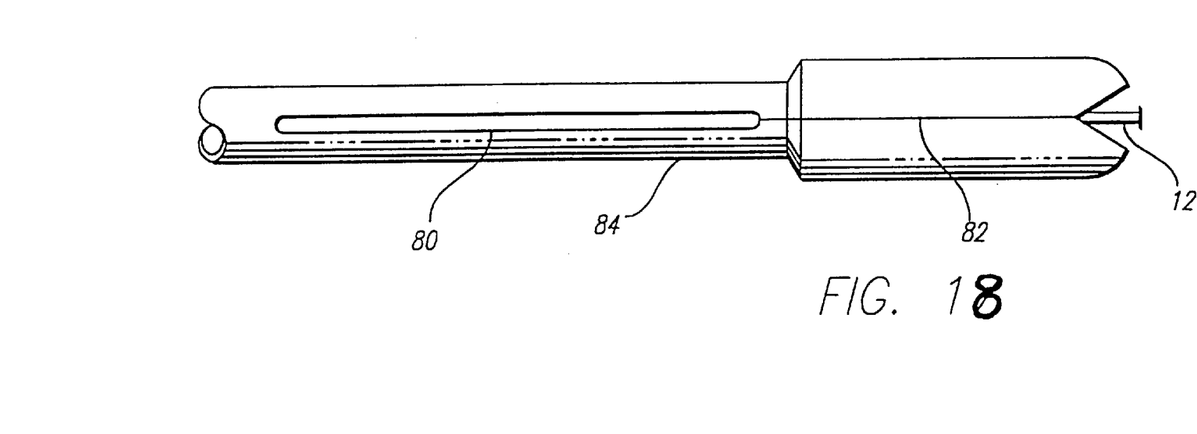
FIG. 18 is a partial, top plan view of the distal end of the stent delivery system depicted in FIG. 17.

FIGS. 17–18 illustrate a rapid exchange variation of the present invention stent delivery system. As shown in FIG. 17, plug 76 is located in the lumen of catheter 10 which prevents guidewire 12 from extending proximally through the catheter lumen. Optional ramp 78 is located on the distal side of plug 76 to force guidewire 12 out of the lumen of catheter 10 and through port 86 in the wall of catheter 10. Guidewire 12 then extends out of slot 80 formed in the wall of sheath 84. Similar to the other embodiments, immobile stop 18 is located proximal to stent 14 to prevent stent 14 from shifting out of position as sheath 84 is withdrawn. As illustrated in FIG. 18, slit 82 extends from port 86 in the wall of sheath 84 to the distal end.

From the foregoing, it will be appreciated that the stent delivery system of the present invention allows self-expanding stents to be deployed while preventing any unwanted axial movement of the stent. The invention is made of materials commonly found in the industry today and is simple to use and easy to manufacture. While particular embodiments of the present invention have been illustrated and described, it will be apparent that various modifications can be made without departing from the spirit and scope of the invention.

What is claimed is:

1. A delivery system for implantation of a self-expanding stent within a body lumen, comprising:
    a delivery assembly including
    an elongated catheter having proximal and distal ends, the distal end configured to receive on an exterior thereof the self-expanding stent;
    an elongated sheath having proximal and distal ends and formed with a lumen to slidably receive the catheter, and having an open-ended receptacle at the distal end for receiving the self-expanding stent;
    a manipulator having a stem axially movable relative to the manipulator, the stem connected to the proximal end of the sheath to adjust an axial position of the sheath relative to the catheter, and wherein the proximal end of the catheter is selectively positioned to engage the manipulator, wherein the manipulator further includes a handle having a hollow tube receiving the proximal end of the sheath, the handle having an elongated slot through which the stem extends, and the handle having a distal end adjustable connected to the proximal end of the sheath; and
    a stop disposed on an exterior of the catheter proximal to the self-expanding stent to prevent the stent from moving proximally during relative movement between the sheath and the catheter; and
    a guide catheter having a proximal end, and formed with a lumen for receiving the delivery assembly therein, and wherein the proximal end is connected to the manipulator.

2. A delivery system as set forth in claim 1, wherein the sheath is formed with a cylindrical body of a first diameter and the receptacle has a second diameter larger than the first diameter.

3. A delivery system as set forth in claim 1, wherein the sheath includes a material selected from the group consisting of polyethylene, nylon, PEEK, or PET.

4. A delivery system as set forth in claim 1, wherein the elongated catheter further comprises an inner lumen within the elongated catheter adapted to receive a guidewire therethrough.

5. A delivery system as set forth in claim 1, wherein the stop includes an annular shape.

6. A delivery system as set forth in claim 1, wherein the elongated catheter includes a sideport for receipt of a guidewire.

7. A delivery system as set forth in claim 1, wherein the elongated slot is formed at the proximal and distal ends with a neck down portion for frictionally engaging the stem.

8. A delivery system as set forth in claim 1, wherein the proximal end of the elongated catheter is connected to the proximal end of the guide catheter, and the connection includes proximal and distal sections wherein the distal section includes an open ended bore that receives the distal end of the proximal section and further includes a rotatable screw that enters the distal section through a port and frictionally engages the proximal section to the distal section.

9. A delivery system as set forth in claim 8, wherein the proximal and distal sections include teeth for resisting lateral movement.

10. A delivery system as set forth in claim 1, wherein the system further comprises connecting the proximal end of the elongated catheter to the proximal end of the guide catheter and the connection includes proximal and distal sections configured with axially disposed, aligned threaded studs, further including a rotatable member with bores for receipt of the studs.

11. A delivery system as set forth in claim 1, wherein the proximal end of the elongated catheter is connected to the proximal end of guide catheter and the connection includes proximal and distal sections wherein an axial bore is formed in the proximal and distal sections and further includes a rotatable screw for engaging threads in the distal section.

12. A delivery system for implanting a self-expanding stent within a body lumen, comprising:
    an elongated catheter having a proximal end and a distal end, wherein the stent is disposed on the catheter at the distal end;
    a sheath having a proximal end and an open distal end, coaxially and slidably disposed over the elongated catheter, wherein the open distal end overlies the stent;
    a manipulator for selectively positioning the proximal end of the catheter, the manipulator further including a radial stem connected to the proximal end of the sheath, wherein movement of the radial stem translates the sheath relative to the catheter;
    wherein the proximal end of the guiding catheter is spaced apart from the manipulator and includes a telescoping spacer connecting the manipulator to the proximal end of the guiding catheter; and
    a guiding catheter having a proximal end and a lumen adapted to receive the sheath, catheter, and stent therein, wherein the proximal end is connected to the manipulator.

13. The delivery system of claim 12, wherein the catheter includes an immobile stop disposed proximal to the stent.

14. The delivery system of claim 12, wherein the manipulator further comprises a distal section connected to the guide catheter and a proximal section connected to the elongated catheter, and wherein the distal section and proximal section are coaxially aligned to telescope.

15. The delivery system of claim 12, wherein the proximal end of the guiding catheter is spaced apart from the manipulator, and the system includes telescoping spacers disposed coaxially over the proximal end of the elongated catheter between the manipulator and the proximal end of the guiding catheter.

16. The delivery system of claim 12, wherein the guiding catheter includes tabs at the proximal end thereof that engage the spacer.

17. The delivery system of claim 14, wherein the telescoping distal section and proximal section include a radially extending threaded screw.

18. A method for delivering for implantation a self-expanding stent within a body lumen, comprising:

provi­ding an elongated catheter having a proximal end and a distal end;

disposing the stent on the catheter at the distal end;

slidably disposing a sheath having a proximal end and an open distal end coaxially over the elongated catheter so that the open distal end at least partially overlies the stent;

providing a manipulator having a stem connected to the proximal end of the sheath;

connecting the proximal end of the catheter to the manipulator;

providing a guiding catheter having a lumen adapted to receive the sheath, catheter, and stent therein;

providing telescoping spacers connected to the manipulator and to the guiding catheter at opposite ends, the telescoping spacers having a threaded screw passing radially therethrough; and displacing the stem to slidably translate the sheath relative to the catheter to expose the stent.

19. The method of claim 18, wherein the step of providing a manipulator further comprises:

providing a manipulator housing receiving the proximal end of the elongated catheter and sheath therethrough;

forming an opening in the manipulator housing; and passing the stem through the opening wherein movement of the stem within the opening translates the sheath relative to the elongated catheter.

20. The method of claim 19, wherein the step of providing telescoping spacers further comprises providing a threaded screw passing axially through one spacer into the other.

21. The method of claim 19, wherein the step of providing telescoping spacers further comprises providing a spacer having external threads engaging an internally-threaded rotatable connecting member at one end, and the rotatable connecting member is rotatably connected to the other spacer at another end.

22. The method of claim 18, wherein the method further comprises providing a stop on the elongated catheter immediately proximal to the stent.

* * * * *

UNITED STATES PATENT AND TRADEMARK OFFICE
CERTIFICATE OF CORRECTION

PATENT NO. : 6,146,415
DATED : November 14, 2000
INVENTOR(S) : Matthew J. Fitz

It is certified that error appears in the above-identified patent and that said Letters Patent is hereby corrected as shown below:

Column 10, claim 12,
Line 46, after "catheter;", add -- and, --.
Delete lines 47 through 50 "wherein......guiding catheter; and".
Line 54, after "manipulator", change "." to -- ; -- and on next line add -- wherein the proximal end of the guiding catheter is spaced apart from the manipulator and includes a telescoping spacer connecting the manipulator to the proximal end of the guiding catheter. --.

Column 10, claim 13,
Line 55, after "wherein the", add -- elongated --.

Signed and Sealed this

Twenty-third Day of October, 2001

*Attest:*

NICHOLAS P. GODICI
*Attesting Officer*    Acting Director of the United States Patent and Trademark Office